United States Patent
Mintz et al.

(10) Patent No.: US 8,591,501 B2
(45) Date of Patent: Nov. 26, 2013

(54) COHERENT FIBER BUNDLE SYSTEM AND METHOD FOR OPHTHALMIC INTERVENTION

(75) Inventors: David Mintz, Mountain View, CA (US); Daniel Palanker, Sunnyvale, CA (US); Gregory Kintz, Ashville, NC (US)

(73) Assignee: Topcon Medical Laser Systems, Inc., Santa Clara, CA (US)

( * ) Notice: Subject to any disclaimer, the term of this patent is extended or adjusted under 35 U.S.C. 154(b) by 136 days.

(21) Appl. No.: 13/042,429

(22) Filed: Mar. 7, 2011

(65) Prior Publication Data
US 2011/0319874 A1    Dec. 29, 2011

Related U.S. Application Data

(60) Provisional application No. 61/311,267, filed on Mar. 5, 2010.

(51) Int. Cl.
*A61F 9/008*   (2006.01)
*A61B 18/22*   (2006.01)
*G02B 6/06*    (2006.01)

(52) U.S. Cl.
USPC .............................................. 606/4; 385/115

(58) Field of Classification Search
None
See application file for complete search history.

(56) References Cited

U.S. PATENT DOCUMENTS

| | | | |
|---|---|---|---|
| 5,688,264 A * | 11/1997 | Ren et al. | 606/15 |
| 7,599,591 B2 | 10/2009 | Andersen et al. | |
| 2008/0015553 A1 | 1/2008 | Zacharias | |
| 2008/0049188 A1 | 2/2008 | Wiltberger et al. | |
| 2009/0005764 A1 * | 1/2009 | Knox et al. | 606/5 |
| 2009/0093798 A1 | 4/2009 | Charles | |

OTHER PUBLICATIONS

International Search Report and Written Opinion received for PCT Patent Application No. PCT/US2011/27453, mailed on Apr. 27, 2011, 7 pages.

* cited by examiner

*Primary Examiner* — Sam Yao
*Assistant Examiner* — Scott T Luan
(74) *Attorney, Agent, or Firm* — Morris & Foerster LLP

(57) ABSTRACT

Systems and processes are described relating to laser-based ophthalmic intervention technologies, and, more specifically, to techniques for creating lesions on an eye using a modular system featuring one or more coherent fiber bundles configured to deliver laser energy to the eye from a separate housing wherein a laser source is located. The subject technology may be utilized to not only separate a patient from certain portions of the hardware, but also to facilitate patterned lesion creation using mobile devices such as LIO and laser endoprobe devices.

24 Claims, 14 Drawing Sheets

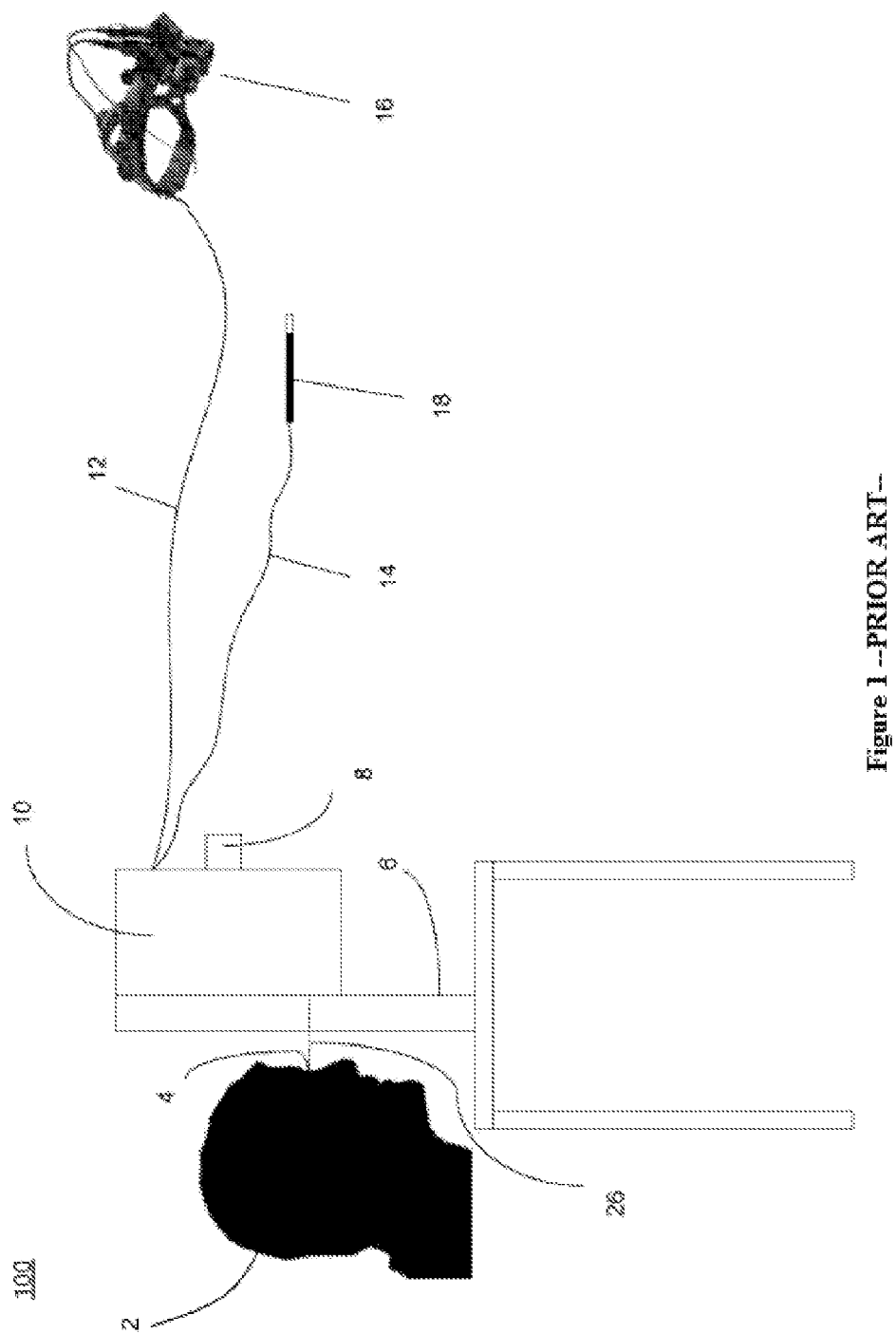
Figure 1 --PRIOR ART--

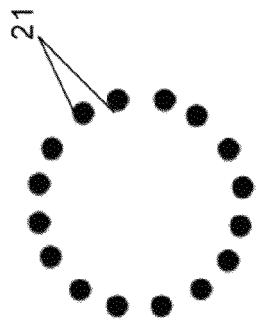
Figure 2C
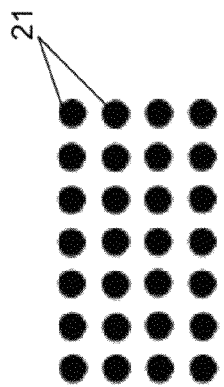
Figure 2E
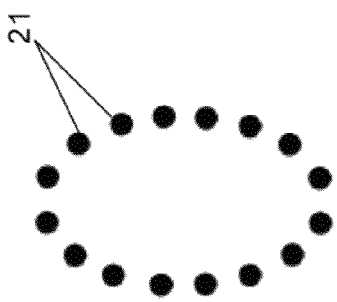
Figure 2B
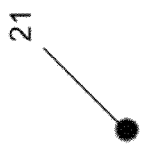
Figure 2A
Figure 2D

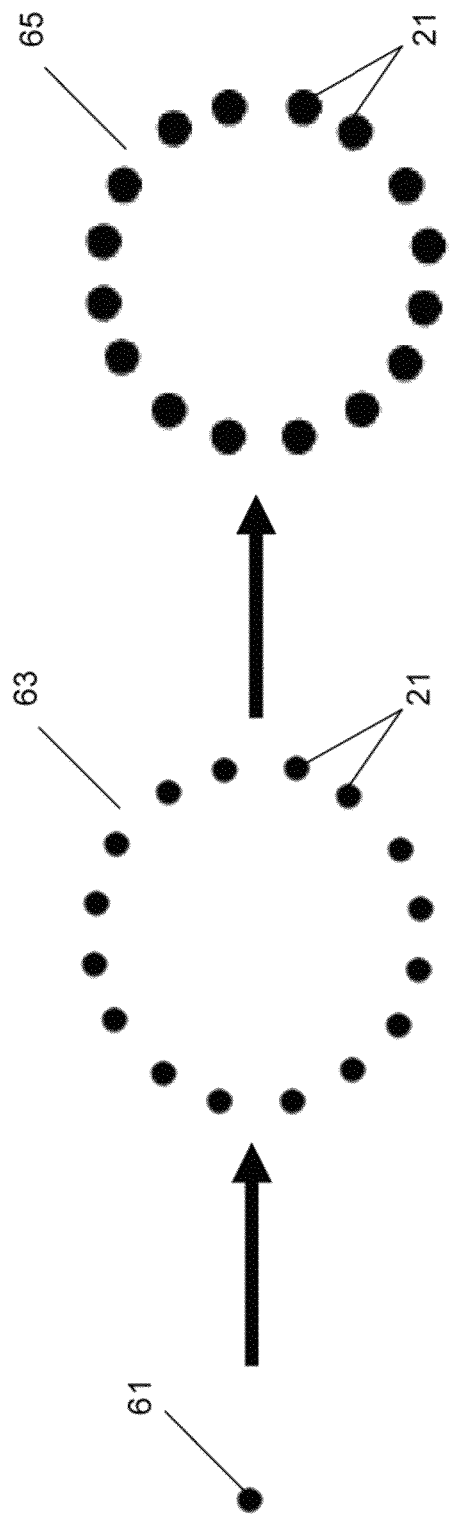

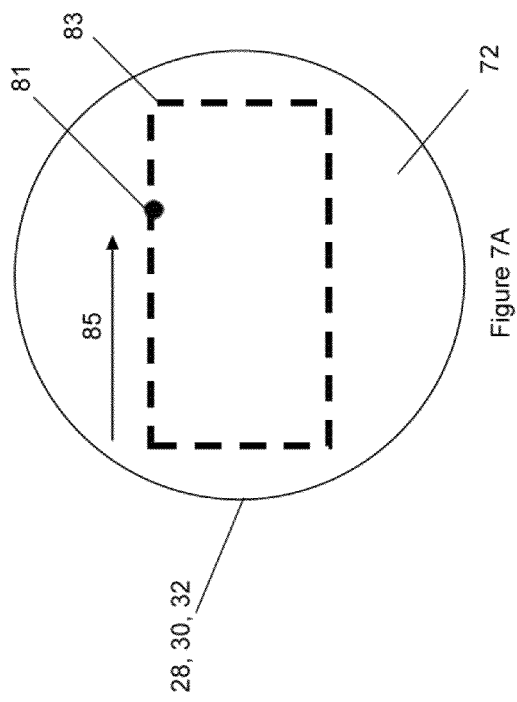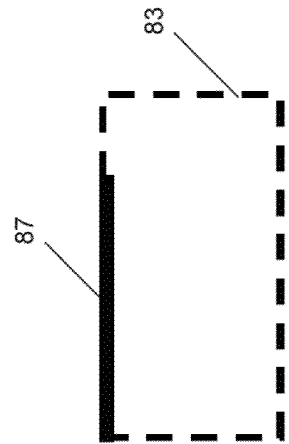

1200

COHERENT FIBER BUNDLE SYSTEM AND METHOD FOR OPHTHALMIC INTERVENTION

BACKGROUND

1. Field

The present disclosure relates to laser-based ophthalmic intervention technologies, and, more specifically, to creating lesions on an eye using a modular system featuring one or more coherent fiber bundles configured to deliver laser energy to the eye from a laser source located in a separate housing.

2. Related Art

Every year, thousands of patients in the United States and other countries undergo laser-based interventional treatments of the eye. Such treatments typically involve the distribution of laser energy to targeted portions of tissue structures to address clinical problems, such as diabetic retinopathy, diabetic macular edema, age-related macular degeneration, or glaucoma. Several types of systems are available for these procedures.

For example, in one type of system, a single treatment beam may be directed through a delivery device, such as a handheld laser endoprobe, head-mounted laser indirect opthalmoscope ("LIO"), or slit lamp, to be aimed or directed by a surgeon or operator to create burn lesions at desired locations. However, these systems lack patterning capability, and instead rely on the surgeon or operator to generate the desired lesion patterns using the single treatment beam via manipulation of the delivery device.

Another type of system features a patterning capability, wherein scanning hardware, which is typically galvanometric, is utilized to create a pattern of lesions on the targeted eye region. For example, FIG. 1 illustrates an exemplary conventional pattern scanning system (100) having a slit lamp apparatus (6) coupled to a scanning/patterning system (10). The scanning/patterning system (10) may be configured to emit a treatment beam (26), which may include either a single treatment beam, such as that shown FIG. 2A, or a patterned treatment beam, such as those shown in FIGS. 2B-E, into the eye (4) of a patient (2) through slit lamp apparatus (6). The treatment beam (26) may be directed by an operator who will typically be positioned adjacent the operator's eyepiece (8). While these types of systems provide patterning capability, they typically require bulky hardware, such as scanning/patterning system (10), located closely adjacent to the patient. This makes the systems difficult to use in situations where the patient is unable to position his or her head upright at the slit lamp table. For example, it would be difficult to use the slit lamp apparatus in an operating room environment where the patient is lying flat on the operating table.

In an attempt to alleviate this problem, some laser-treatment systems, such as that shown in FIG. 1, include a handheld endoprobe (18) or LIO (16) coupled to the scanning/patterning system (10) by a conventional multi-mode fiber (12, 14—typically directed to either such fiber by a beam splitter). These devices, however, are generally capable of delivering only a single treatment beam. This is because multi-mode fibers typically comprise a single piece of glass fiber with cladding material. As a result, multi-mode fibers (12, 14) are unable to maintain the spatial relationship between areas of laser energy concentration (21) of a patterned treatment beam. In other words, multi-mode fibers (12, 14) are unable to reproduce the patterns shown in FIGS. 2B-E at a distal end of the fiber when applied to a proximal end of the fiber. Instead, the areas of laser energy concentration (21) may mesh together to form a single composite beam when transmitted through multi-mode fibers (12, 14). As a result, endoprobe (18) and LIO (16) lack the patterning capability offered by the slit lamp apparatus (6).

It should be appreciated that FIG. 1 illustrates a simplified system view of an exemplary conventional pattern scanning system. As such, conventional systems may include slight variations to what is shown in FIG. 1, for instance, other systems may instead include a laser source located separately from the scanning/patterning system (10) or may include a laser source located within the slit lamp table. However, to deliver a patterned treatment beam, those systems require scanning/patterning hardware located near the delivery device.

Thus, a system capable of directing patterns through a slit lamp, LIO, endoprobe, and the like, while functioning without the present level of hardware positioned near the patient in the slit lamp configuration, is desired.

SUMMARY

In one exemplary embodiment, a system for laser treatment of an eye of a patient is provided. The system includes a coherent fiber bundle comprising a first end and a second end; a first subsystem coupled to the first end of the coherent fiber bundle, the first subsystem configured to: generate a patterned treatment beam comprising at least two separate areas of laser energy concentration, wherein a size of the at least two separate areas of laser energy concentration and a pattern formed by the at least two separate areas of laser energy concentration are adjustable by the first subsystem; and direct the patterned treatment beam to the first end of the coherent fiber bundle; and a second subsystem coupled to the second end of the coherent fiber bundle, the second subsystem configured to: receive the patterned treatment beam from the second end of the coherent fiber bundle; and transmit the patterned treatment beam to the eye of the patient.

In some embodiments, the second subsystem is incorporated within a slit lamp, endoprobe, or laser indirect opthalmoscope ("LIO"). In other embodiments, the second subsystem is coupled to a slit lamp, endoprobe, or LIO.

In one exemplary embodiment, the first subsystem is configured to direct the patterned treatment beam to a portion of the first end of the coherent fiber bundle, wherein the second subsystem is configured to receive the patterned treatment beam from a portion of the second end of the coherent fiber bundle, and wherein the portion of the second end of the coherent fiber bundle corresponds to the portion of the first end of the coherent fiber bundle. In other embodiments, a relative location of the portion of the first end of the coherent fiber bundle with respect to the first end of the coherent fiber bundle is substantially the same as a relative location of the portion of the second end of the coherent fiber bundle with respect to the second end of the coherent fiber bundle.

In another exemplary embodiment, the treatment beam is substantially at a non-visible wavelength and has a power in the range of 30 mW to 2 W.

In another exemplary embodiment, the first subsystem comprises: a laser source configured to generate a laser beam; a spot size selector configured to: receive the laser beam; and adjust the size of the at least two separate areas of laser energy concentration by adjusting the size of the laser beam; and scanning hardware configured to: receive the size-adjusted laser beam from the spot size selector; and generate the pattern formed by the at least two separate areas of laser energy concentration by selectively redirecting the received size-adjusted laser beam. In other embodiments, the first subsystem further comprises an interface for coupling to an LIO or endoprobe via a multi-mode fiber, the interface configured to transmit a single treatment beam through the multi-mode fiber.

In another exemplary embodiment, the laser source is further configured to generate an alignment beam having an average power of less than 1.2 mW and substantially at a visible wavelength. The scanning hardware may comprise a collimating lens and a scanning device. The scanning device may comprise a galvanometer, micro-electro-mechanical ("MEMS") device, or rotating polygon.

In another exemplary embodiment, the first subsystem is contained in a first housing that is physically separate from a second housing containing the second subsystem.

In other exemplary embodiments, processes are provided for operating the systems for laser treatment of an eye of a patient.

BRIEF DESCRIPTION OF THE DRAWINGS

FIG. 1 illustrates aspects of an exemplary laser intervention system for the eye, wherein scanning hardware is housed adjacent to the patient.

FIGS. 2A-E illustrate various exemplary treatment beam patterns that may be used to treat a patient.

FIGS. 6A-C illustrate an exemplary sequence of treatment beam patterns that may be output using a modular laser intervention system like that illustrated in FIGS. 3 and 5.

FIGS. 7A-B illustrate a single treatment beam being used to generate a lesion pattern using a modular laser intervention system like that illustrated in FIGS. 3 and 5.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the present technology. Thus, the disclosed technology is not intended to be limited to the examples described herein and shown, but are to be accorded the scope consistent with the claims.

As described above, laser-treatment systems are commonly used to deliver laser energy to targeted portions of the eye in order to create lesions or increase the temperature of the eye at desired locations. The laser energy may be delivered as a single treatment beam having a single area of laser energy concentration (21) to create a single lesion on the eye, for example, as shown in FIG. 2A. Alternatively, the laser energy may be delivered as a patterned treatment beam having multiple separate areas of laser energy concentration (21) to create multiple lesions on the eye, for example, as shown in FIGS. 2B-E. It should be appreciated that the illustrated patterns are provided only as examples, and that any pattern may be generated depending on the desired application.

Figure 3:
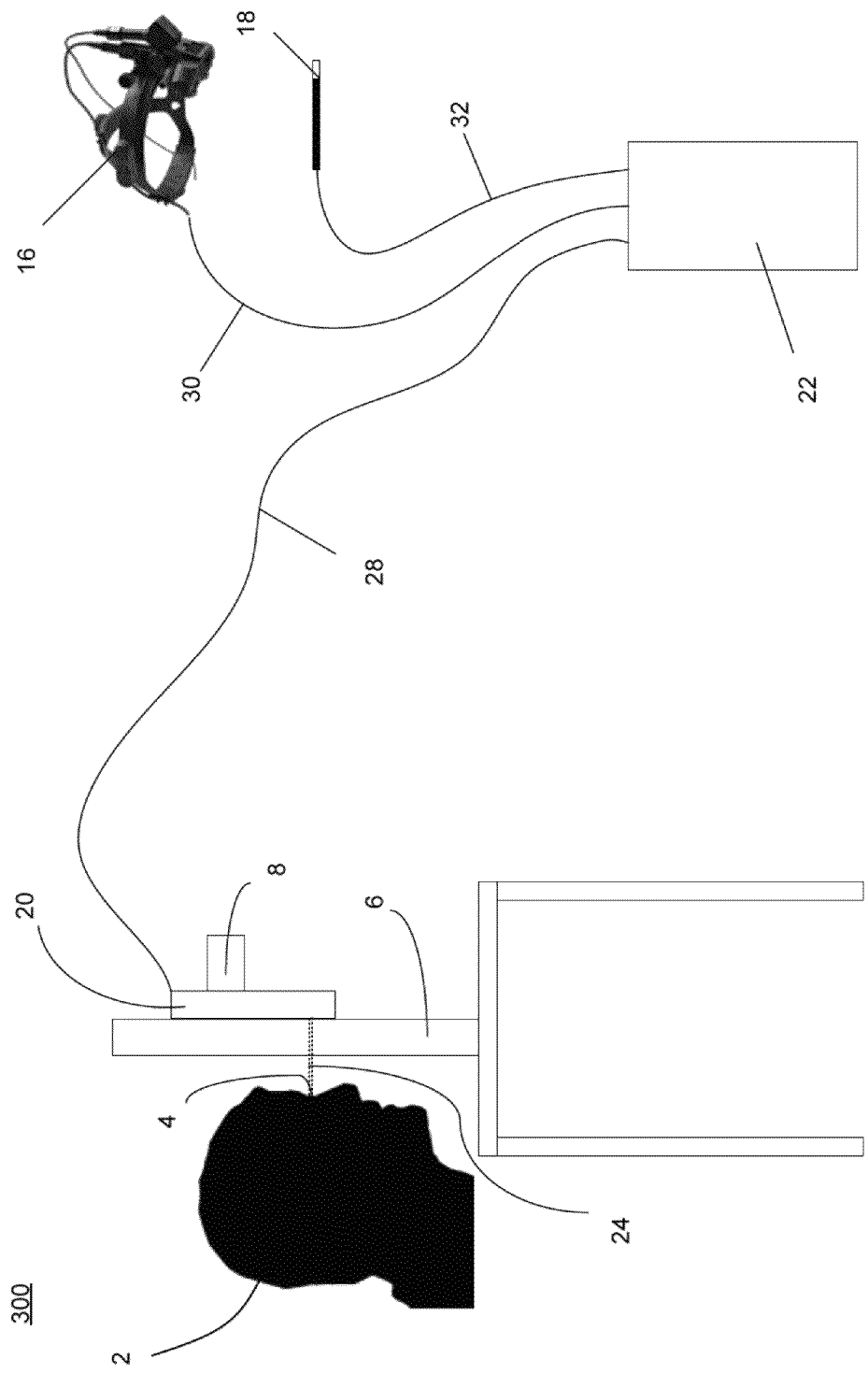
FIG. 3 illustrates aspects of an exemplary modular laser intervention system for the eye.

FIG. 3 illustrates an exemplary modular laser-treatment system (300) that, through the use of coherent fiber bundles, is capable of delivering single treatment beams and patterned treatment beams through various types of delivery devices while requiring minimal hardware located near the delivery devices.

Figure 4A:
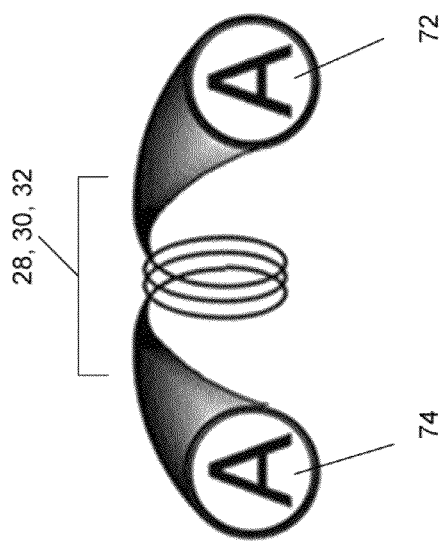
FIGS. 4A-D illustrate properties of a coherent fiber bundle that may be utilized with a modular laser intervention system like that illustrated in FIG. 3.

Coherent fiber bundles, unlike conventional multi-mode fibers, comprise many (e.g., between 1,500 and 100,000) optical fibers bundled together to form a transmission device having pixels equal to the number of bundled optical fibers. This allows an image or pattern of irradiation mapped to a proximal face of the bundles to be duplicated at a distal face. For example, FIG. 4A illustrates the notion of pattern or image transmission from a proximal face (72) of the coherent fiber bundle (28, 30, 32) to a distal face (74) of the bundle (28, 30, 32). Note that the image of the letter "A" at the distal face (74) is identical, or at least substantially similar, to the image applied to the proximal face (72).

The ability to duplicate an image or pattern of irradiation is an important feature of coherent fiber bundles that allow them to be used in the present disclosure for laser-treatment of the eye. Specifically, when performing laser treatment, it is important that an operator or surgeon be able to carefully control the wavelength, power, duration, size, pattern (e.g., spot arrangement, spot-to-spot spacing, etc), and the like, of the treatment beam applied to the eye. Additionally, the delivery device should deliver a consistent power profile for each delivered laser pulse. In the case of a pattern scanning system, it is important that each spot in a pattern have the laser energy delivered in a consistent manner. Significant distortion of these properties by the delivery device or transmission medium may result in improper application of laser energy to the eye.

Figure 4B:
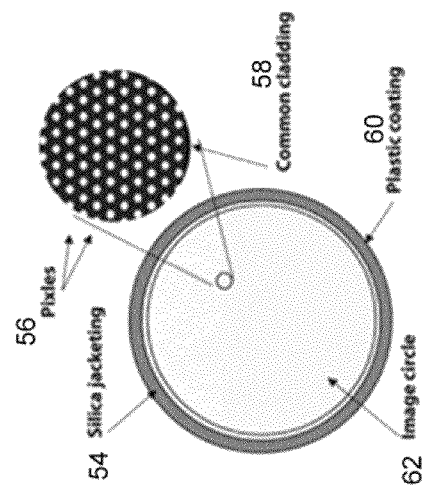

FIG. 4B illustrates a cross sectional view of one exemplary embodiment of a suitable coherent fiber bundle (28, 30, 32), depicting the image circle (62), silica jacketing (54), outer polymer or plastic coating (60), and pixels or individual fibers (56), which are held adjacent to each other with a common cladding (58). These coherent fiber bundles typically have between 1,600 and 100,000 fibers at 140 to 1,500 µm. In one embodiment, the coherent fiber bundle (28, 30, 32) may have an image circle diameter of about 790 microns, a fiber bundle outer diameter of about 850 microns, an overall diameter (with the outer coating) of about 950 microns, about 30,000 individual fibers, a lattice defect of less than about 0.1%, a relatively high numerical aperture of about 0.4, a minimum bend radius (without significant side loss or breakage) of about 50 millimeters, and a length that can be selected depending upon the particular installation—such as about 2, 3, 4, or more meters.

In other embodiments, coherent fiber bundles (28, 30, 32) may include leached image bundles having multiple fibers with individual cladding, where the fibers are aligned at the bundle ends and held in place with a ferrule. These types of coherent fiber bundles typically have between 10,000 and 18,000 fibers at 670 to 1650 μm.

While specific exemplary characteristics are provided above for coherent fiber bundles (28, 30, 32), it should be appreciated that coherent fiber bundles having other characteristics may be used depending on the desired application. Suitable coherent fiber bundles (28, 30, 32) are available from manufacturers such as Fujikura, Inc., Sumitomo, Inc., National Aperture, Inc. of Salem, N.H., SCHOTT, and Mitsubishi, Inc.

Referring back to FIG. 3, in contrast to scanning/patterning system (10) of conventional pattern scanning system (100), the scanning/patterning components of modular laser-treatment system (300) are separated into two subsystems (20, 22). Specifically, modular laser-treatment system (300) includes proximal subsystem (22) containing a laser source, spot size selection hardware, and the scanning hardware required to generate single and patterned treatment beams. Modular laser-treatment system (300) further includes one or more distal subsystems (20) containing the hardware required to receive and deliver the treatment beams generated by the proximal subsystem (22).

Modular laser-treatment system (300) may further include any number of distal subsystems (20) forming a delivery device, such as handheld laser endoprobe (18), LIO (16), slit lamp adapter (20), and a slit lamp apparatus incorporating a distal subsystem (20) (not shown), each device configured to deliver a treatment beam received from proximal subsystem (22). For example, a distal subsystem (20) is shown coupled to slit lamp apparatus (6) in FIG. 3, with the distal subsystem (20) acting as a slit lamp adapter. In other embodiments, slit lamp apparatus (6) may instead incorporate the components of distal subsystem (20) within the apparatus. Additionally, while not shown, it should be appreciated that additional distal subsystems (20) may be included within or coupled to each of endoprobe (18) and LIO (16).

Figure 4C:
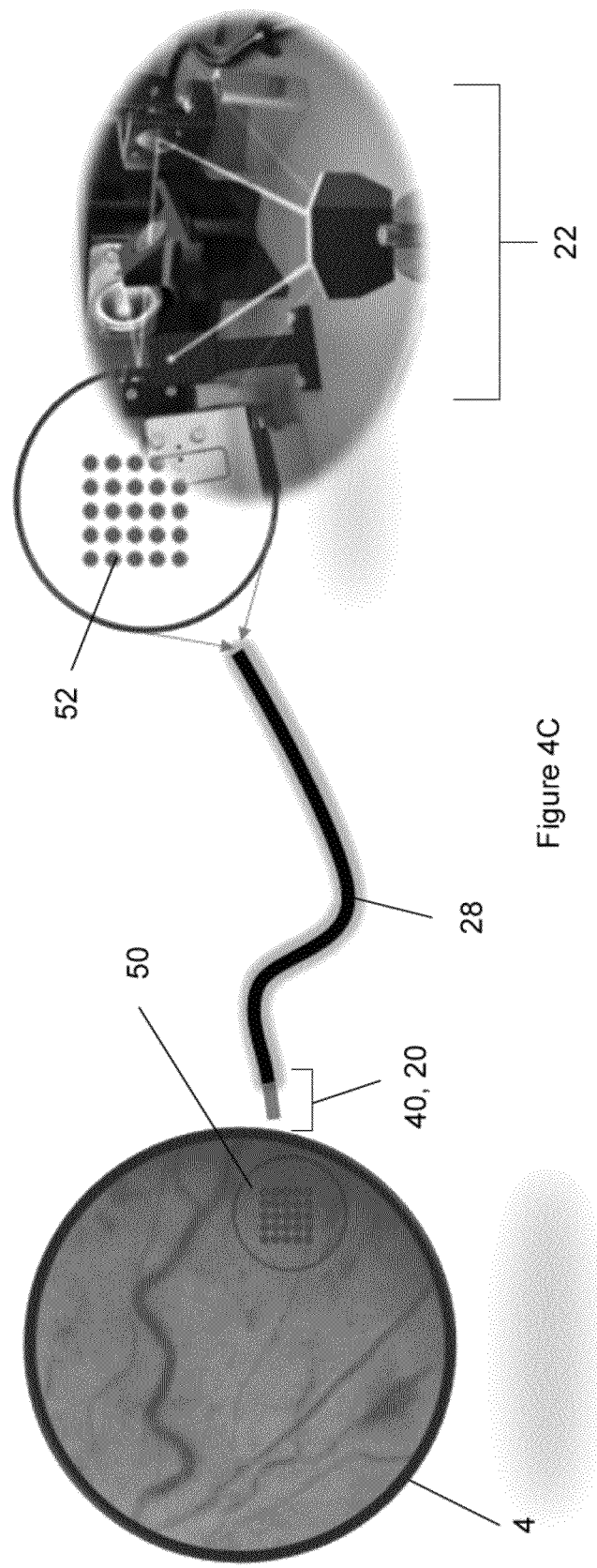
Figure 4D:
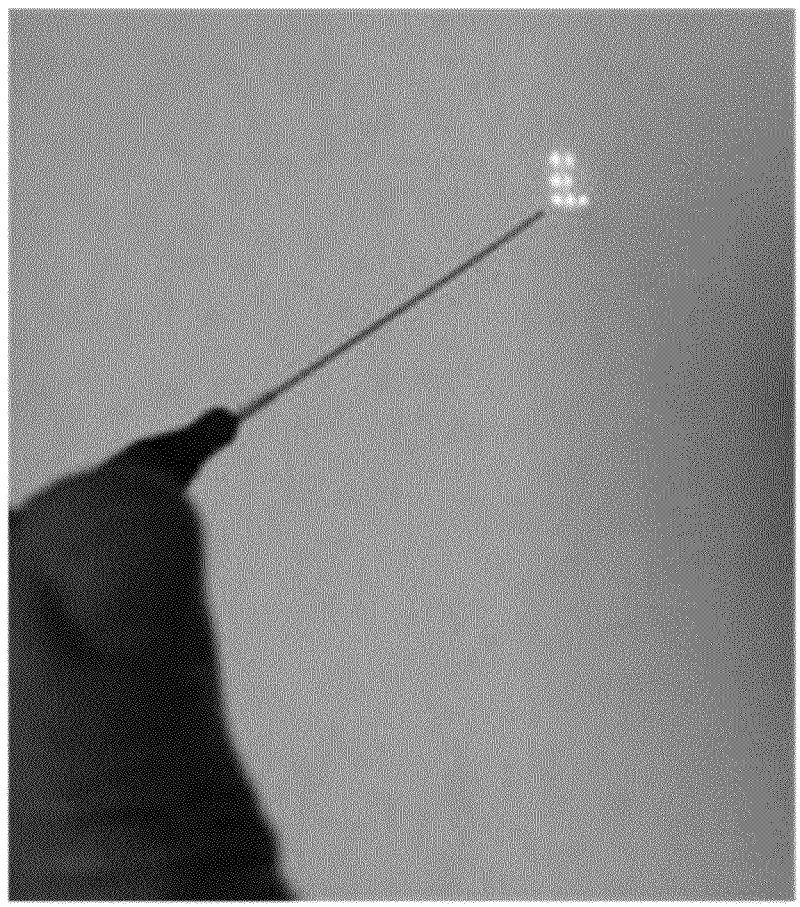

As shown in FIG. 3, distal subsystems (20) may be coupled to proximal subsystem (22) through coherent fiber bundles (28, 30, 32). Coherent fiber bundles (28, 30, 32), as discussed above, are capable of duplicating an image or pattern of irradiation mapped to the proximal face of the bundles to a distal face of the bundles. This allows proximal subsystem (22), which includes the bulky spot size selection hardware and scanning/patterning system hardware, to be physically separated from the distal subsystem (20), while still being able to transmit a treatment beam to the delivery devices for administering to the patient. For example, as shown in FIG. 4C, a patterned treatment beam (52) produced by the proximal subsystem (22) may be directed via coherent fiber bundles (28, 30, 32) to a distal subsystem (20) to create a patterned lesion (50) on an eye (4). FIG. 4D shows a photo of a patterned treatment beam being delivered through a coherent fiber bundle and endoprobe configured in a manner similar to the arrangement shown in FIG. 4C.

In some embodiments, the proximal subsystem (22) and distal subsystem (20) may be contained in separate housings and coupled together via a coherent fiber bundle (28). Since the distal subsystem (20) of system (300) is substantially smaller than the scanning/patterning system (10) of system (100), this configuration desirably decreases the amount of hardware required near the delivery device, and consequently, decreases the amount of hardware required near the patient.

Additionally, since the slit lamp (6), endoprobe (18), and LIO (16) may each include or be coupled to a distal subsystem (20), coherent fiber bundles (28, 30, 32) allow the proximal subsystem (22) to distribute a patterned treatment beam to a patient's eye not only through slit lamp (6), but also through endoprobe (18) and LIO (16) via the distal subsystems (20).

Figure 5:
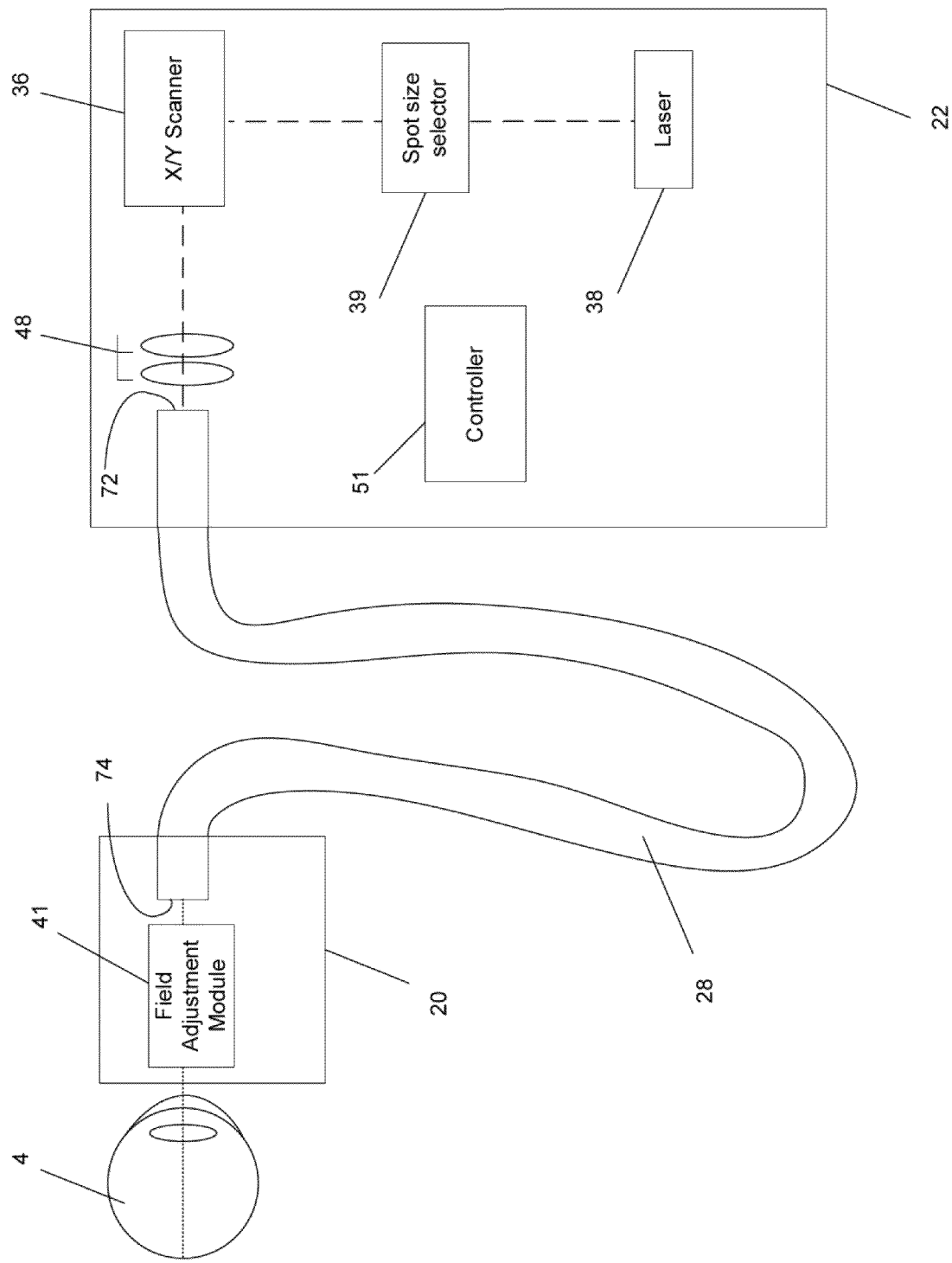
FIG. 5 illustrates aspects of an exemplary modular laser intervention system for the eye.

FIG. 5 illustrates a more detailed view of aspects of modular laser-treatment system (300). As shown in FIG. 5, proximal subsystem (22) includes laser source (38) configured to transmit a single laser beam. In some embodiments, laser source (38) may include an Argon laser, Krypton laser, diode laser, Nd-YAG laser, or any other pulsed or continuous wave laser suitable for eye therapy. The beam generated by laser source (38) may be continuous or pulsed at a duration from about 1 ms to about 1 second, may have a power from about 30 mW to about 2 W, may have a diameter from about 50 μm to about 500 μm (e.g., about 60 μm or about 400 μm), and may have a wavelength in the visible spectrum (e.g., 532 nm, 561 nm, 577 nm, 647 nm, 659 nm, or 670 nm) or a wavelength in the non-visible spectrum (e.g., 810 nm).

In some embodiments, laser source (38) may generate a low-power beam having an average power of less 1.2 mW and at a visible wavelength (e.g., 635 nm or 640 nm) to be used as an alignment beam. The operator of modular laser-treatment system (300) may use the alignment beam to the aim the delivery device by positioning the alignment beam over the target site of the patient prior to delivering a treatment beam. Once the delivery device is positioned over the target site, the operator may trigger modular laser-treatment system (300), causing laser source (38) to instead deliver a treatment beam in substantially the same location as the previously delivered alignment beam.

Activation of laser source (38) (e.g., pulse duration, power, wavelength, etc.) may be controlled by a controller (51). Controller (51) may include a general or special purpose processor configured to control the various components of proximal subsystem (22), such as laser source (38), spot size selector (39), and scanning hardware (36). Controller (51) may further include a computer-readable storage medium for providing instructions to the processor for execution. Such instructions, generally referred to as "computer program code" (which may be grouped in the form of computer programs or other groupings), when executed, enable the processor to perform features or functions of embodiments of the apparatus and processes described herein. In some examples, the computer-readable storage medium may include a main memory, such as a random access memory (RAM) or other dynamic memory, for storing information and instructions to be executed by a processor. The main memory may also be used for storing temporary variables or other intermediate information during execution of instructions to be executed by the processor. The computer-readable storage medium may likewise include a read-only memory ("ROM") or other static storage device coupled for storing static information and instructions for the processor.

Proximal subsystem (22) may further include spot size selector (39) for adjusting the "spot size" of the treatment beam delivered to the patient. The "spot size" of a beam refers to the size of the areas of laser energy concentration (21) of the beam. Spot size selector (39) may include continuous magnification change optics, a rotating turret of different magnification optics, or any other arrangement of optics used to change magnification known to those skilled in the art. Spot size selector (39) may be configured to receive the single laser beam from laser source (38) and selectively adjust the size of the single laser beam by varying the selected magnification. The single laser beam may be aimed at spot size selector (39), may be directed to spot size selector (39) by an optical fiber, or may be directed to the spot size selector (39) from a free-space laser source with relay or collimating optics. Since the single laser beam is used to generate the treatment beam output by proximal subsystem (22), spot size selector (39) may be used to adjust the "spot size" of the treatment beam delivered to the patient by adjusting the size of the single laser beam generated by laser source (38). The selected magnification of spot size selector (39) may be controlled by controller (51).

Proximal subsystem (22) further includes scanning hardware (36) that uses the size-adjusted single laser beam from spot size selector (39) to generate a single treatment beam or a patterned treatment beam. In some embodiments, the scanning hardware (36) may include a collimating lens (not shown), first and second scanning devices (not shown), such as galvanometers, MEMS devices, rotating polygons, or the like, and an optional set of relay lenses (not shown) separating the first and second scanning devices. The collimating lens may be configured to receive the size-adjusted single laser beam from spot size selector (39). The output of the collimating lens may be a collimated beam that may be directed to a first scanning device, such as a galvanometer, MEMS device, rotating polygon, or the like. The position of the first scanning device may be precision controlled using a computerized control system (e.g., controller (51)) to aim the collimated beam to a second scanning device, such as a second galvanometer, MEMS device, rotating polygon, or the like. The second scanning device may be configured to respond to the computerized control system (e.g., controller (51)) to adjust the collimated beam in a direction orthogonal to the direction of adjustment of the first scanning device. In other words, the pair of scanning devices may be utilized to adjust the X-Y Cartesian position of the treatment beam (26) relative to the microscope objective (48) and proximal face (72) of the coherent fiber bundle (28). In some examples, this may be done to move a single treatment beam relative to the microscope objective (48) and proximal face (72). In other examples, the scanning devices may be synchronized with the pulses generated by the laser source (38) and cycled through several positions relatively quickly to produce a patterning effect having multiple areas of laser energy concentration (21), such as those shown in FIGS. 2B-E. In the depicted system, the beam exiting the second scanning device of scanning hardware (36) is directed through a specialized set of lenses known as a microscope objective (48) and directly at the open cross-sectional face of the proximal end (72) of a coherent fiber bundle (28). The microscope objective (48) may have a low numerical aperture to maximize power efficiency.

Modular laser-treatment system (300) further includes a distal subsystem (20) for receiving and delivering the laser output generated by the proximal subsystem (22). The distal subsystem (20) may comprise minimal hardware required to receive and deliver the patterned treatment beam generated by the proximal subsystem (22) to the patient. For example, distal subsystem (20) may include interfaces for the coherent fiber bundle (28) and a field adjustment module (41) for adjusting the field of view of distal subsystem (20). Field adjustment module (41) may include continuous magnification change optics, a rotating turret of different magnification optics, or any other arrangement of optics used to change magnification known to those skilled in the art. In some embodiments, distal subsystem (20) may include a controller (not shown) similar to controller (51) to select the field of view by setting the magnification of field adjustment module (41). In other embodiments, the selection may be made manually by the user. Field adjustment module (41) may be configured to receive the treatment beam from coherent fiber bundle (28) and selectively adjust the field of view of distal subsystem (20) by varying the selected magnification. For example, by increasing the magnification, field adjustment module (41) may decrease the field of view, thereby increasing the pixel density of the treatment beam output by distal subsystem (20). Similarly, by decreasing the magnification, field adjustment module (41) may increase the field of view that may be addressed by the distal subsystem (20). It should be appreciated that while FIG. 5 shows the coupling between the proximal subsystem (22) and the distal subsystem (20) through coherent fiber bundle (28), a similar coupling may be used between the proximal subsystem (22) and distal subsystems (20) coupled to or included within mobile devices, such as LIO (16) and endoprobe (18), through coherent fiber bundles (30, 32).

In this configuration, modular laser-treatment system (300) may generate and transmit patterned treatment beams having any desired pattern and spot size to a delivery device via coherent fiber bundles (28, 30, 32) by adjusting the laser output of proximal subsystem (22). This may be done without modifying the physical arrangement of components in modular laser-treatment system (300). For example, FIGS. 6A-C illustrate a sequence of patterns that may be generated and output by a delivery device without moving the delivery device or components within the delivery device.

Starting at FIG. 6A, proximal subsystem (22) may generate and project a single treatment beam (61) onto a location on the proximal face (72) of a coherent fiber bundle (28, 30, 32). The position of the single treatment beam (61) on the proximal face (72) may be controlled using the scanning hardware (36) of the proximal subsystem (22), while the spot size may be adjusted using spot size selector (39). In response, the coherent fiber bundle (28, 30, 32) may output the single treatment beam (61) from a location on the distal face (74) that corresponds to the input location on the proximal face (72).

Proximal subsystem (22) may then, as shown in FIG. 6B, generate and project a patterned treatment beam (63) onto the proximal face (72) of the coherent fiber bundle (28, 30, 32). In this example, the patterned treatment beam (63) has the same spot size as the single treatment (61) of FIG. 6A, but instead includes multiple concentrated areas of laser energy arranged in a circular pattern. The patterned treatment beam (63) may be generated by quickly cycling the first and second scanning devices of scanning hardware (36) through multiple positions, where each position corresponds to a different area of concentrated laser energy. As a result, the coherent fiber bundle (28, 30, 32) may output patterned treatment beam (63) from the locations on distal face (74) that correspond to the input locations on the proximal face (72).

Proximal subsystem (22) may then, as shown in FIG. 6C, generate and project another patterned treatment beam (65) onto the proximal face (72) of the coherent fiber bundle (28, 30, 32). The patterned treatment beam (65) has the same number of concentrated areas of laser energy arranged in the same circular pattern as patterned treatment beam (63) of FIG. 6B, but in this example, has larger spot sizes. The patterned treatment beam (65) may be generated by quickly cycling the first and second scanning devices of scanning hardware (36) through multiple positions in the same manner as required to create patterned treatment beam (63). However, spot size selector (39) may be used to enlarge the spot size of the patterned treatment beam (65). As a result, the coherent fiber bundle (28, 30, 32) may output patterned treatment beam (65) from the locations on distal face (74) that correspond to the input locations on the proximal face (72).

In a similar manner, modular laser-treatment system (300) may trace a continuous pattern using a single treatment beam. For example, FIG. 7A shows a single treatment beam (81) projected onto the proximal end (72) of a coherent fiber bundle (28, 30, 32) by proximal subsystem (22). The single treatment beam (81) is moved along rectangular pattern (83) by scanning hardware (36) within the proximal subsystem (22). As the single treatment beam (81) is moved in the direction indicated by arrow (85), a beam is output at the distal end of the coherent fiber bundle (28, 30, 32) at the corresponding position of the bundle face. Thus, the pattern traced on the proximal end (72) of a coherent fiber bundle (28, 30, 32) is reproduced at the distal end. FIG. 7B illustrates the lesion (87) created by applying the output of the coherent fiber bundle (28, 30, 32) to a target site when the single treatment beam (81) is projected into the bundle as shown in FIG. 7A. Thus, modular laser-treatment system (300) may generate a patterned lesion using a single treatment beam without requiring the delivery device or components within the delivery device to be moved. In other words, the delivery device may be positioned stationary relative to the patient's eye, while the proximal subsystem (22) moves the treatment beam within coherent fiber bundle (28, 30, 32) to generate the desired lesion pattern.

Figure 8:
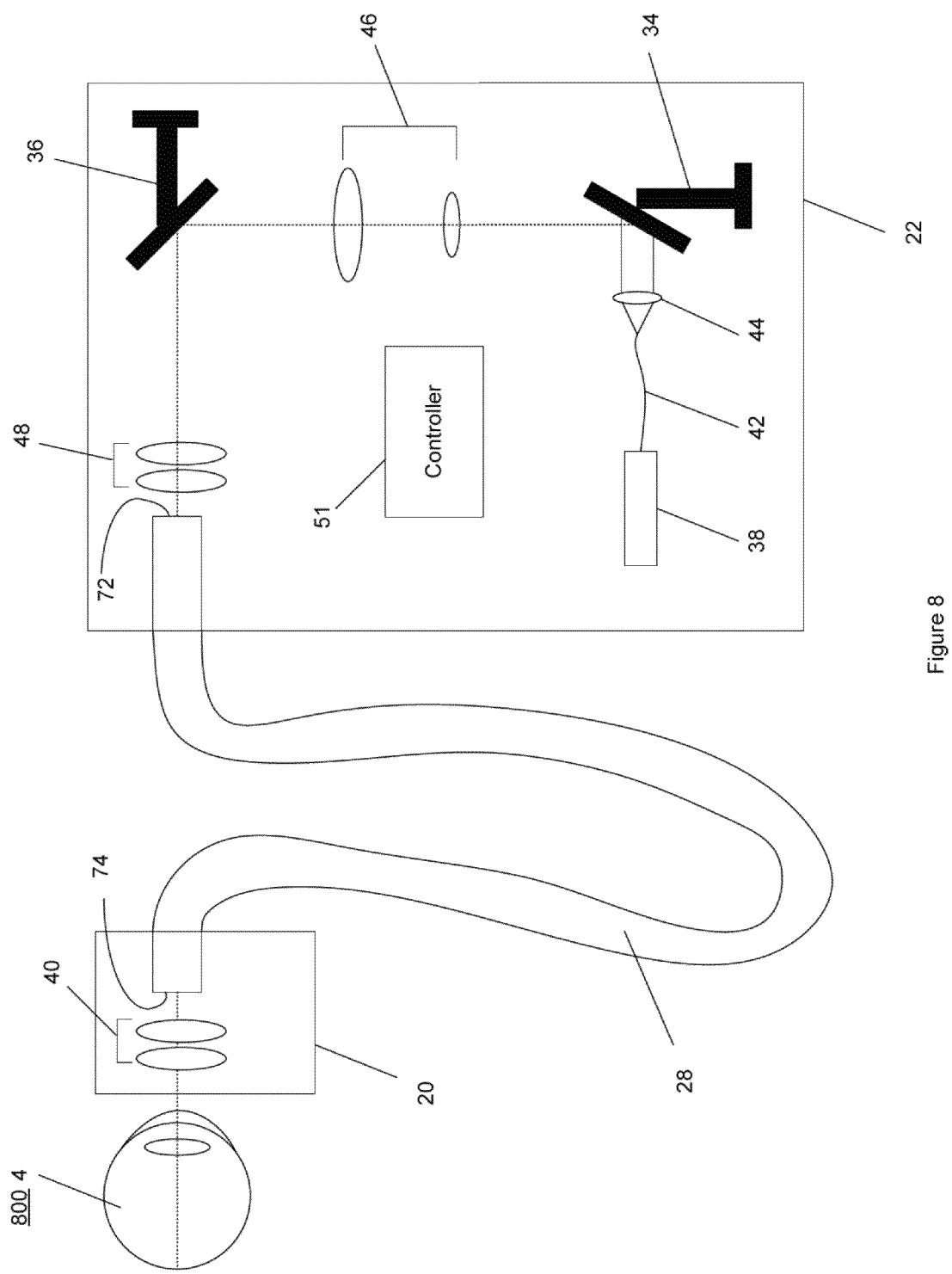
FIG. 8 illustrates aspects of another exemplary modular laser intervention system for the eye.

FIG. 8 illustrates another exemplary modular laser-treatment system (800) that is similar to modular laser-treatment system (300), except that modular laser-treatment system (800) lacks the spot size selection and field of view adjustment capability of modular laser-treatment system (300). Similar to modular laser-treatment system (300), modular laser-treatment system (800) includes a proximal subsystem (22) and a distal subsystem (20).

Proximal subsystem (22) includes laser source (38) configured to transmit a single laser beam a laser source (38). The activation of laser source (38) (e.g., pulse duration, power, wavelength, etc.) may be controlled by controller (51). Proximal subsystem (22) further includes scanning hardware that uses the single beam generated by laser source (38) to generate a single treatment beam or a patterned treatment beam. The scanning hardware may include a collimating lens (44), first and second scanning devices, such as galvanometers (34, 36), MEMS devices, rotating polygons, or the like, and a set of relay lenses (46). The collimating lens (44) may be configured to receive the single laser beam produced by laser source (38) through an optical fiber (42). The output of the collimating lens (44) may be a collimated beam that may be directed to a scanning device, such as a galvanometer (34), MEMS device, rotating polygon, or the like. The position of the first galvanometer (34) may be precision controlled using a computerized control system (e.g., controller (51)) to aim the collimated beam through a set of relay lenses (46) to a second scanning device, such as a second galvanometer (36), MEMS device, rotating polygon, or the like. The second scanning device may be configured to respond to the computerized control system (e.g., controller (51)) to adjust the collimated beam in a direction orthogonal to the direction of adjustment of the first galvanometer (34). In other words, the pair of galvanometers (34, 36) may be utilized to adjust the X-Y Cartesian position of the treatment beam (26) relative to the microscope objective (48) and proximal face (72) of the coherent fiber bundle (28). In some examples, this may be done to move a single treatment beam relative to the microscope objective (48) and proximal face (72). In other examples, the scanning devices may be synchronized with the pulses generated by the laser source (38) and cycled through several positions relatively quickly to produce a patterning effect having multiple areas of laser energy concentration (21), such as those shown in FIGS. 2B-E.

Modular laser-treatment system (800) further includes a distal subsystem (20) similar to that of modular laser-treatment system (300), except that field adjustment module (41) is replaced by projection optics (40) (e.g., a turning mirror). Distal subsystem (20) may receive the treatment beam from proximal subsystem (22) and output the treatment beam in a similar manner as described above for laser-treatment system (300).

Figure 9:
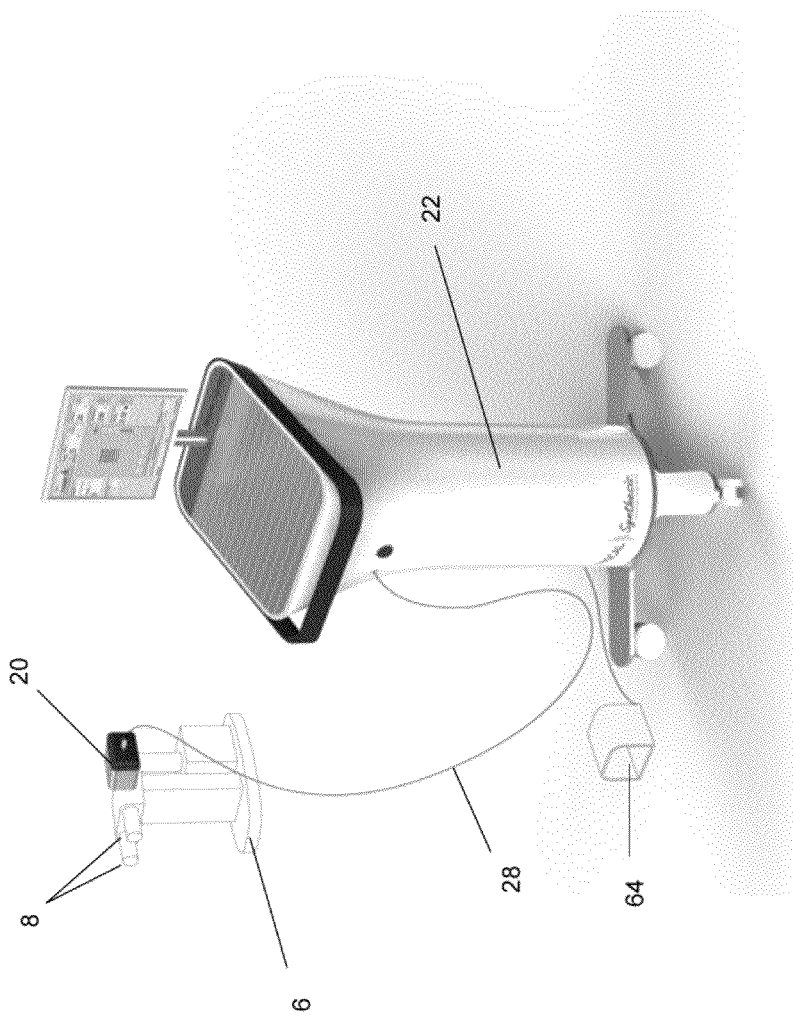
FIG. 9 illustrates aspects of an exemplary laser intervention system for the eye, wherein laser energy may be directed to a slit lamp using a coherent fiber bundle.

FIG. 9 illustrates an exemplary system configuration (900) featuring a movably positioned proximal subsystem (22) coupled to a distal subsystem (20) with a coherent fiber bundle (28). The distal subsystem (20) is coupled to a slit lamp configuration (6) and may be utilized to deliver single treatment beams and patterned treatment beams to a patient's eye. A foot pedal (64) is depicted for triggering various states of the proximal subsystem (22), such as laser irradiation ON/OFF. Alternatively, in other embodiments, system configuration (900) may include a graphical user interface ("GUI") instead of foot pedal (64) for triggering the various states of the proximal subsystem (22). System configuration (900) may further include interfaces for supporting mobile devices, such as an LIO, endoprobe, or the like. The mobile devices may be coupled to the proximal subsystem (22) by coherent fiber bundles to deliver single treatment beams and patterned treatment beams to a patient's eye. Alternatively, the mobile devices may be coupled to proximal subsystem (22) by conventional multi-mode fibers to provide conventional single-beam treatment.

Figure 10:
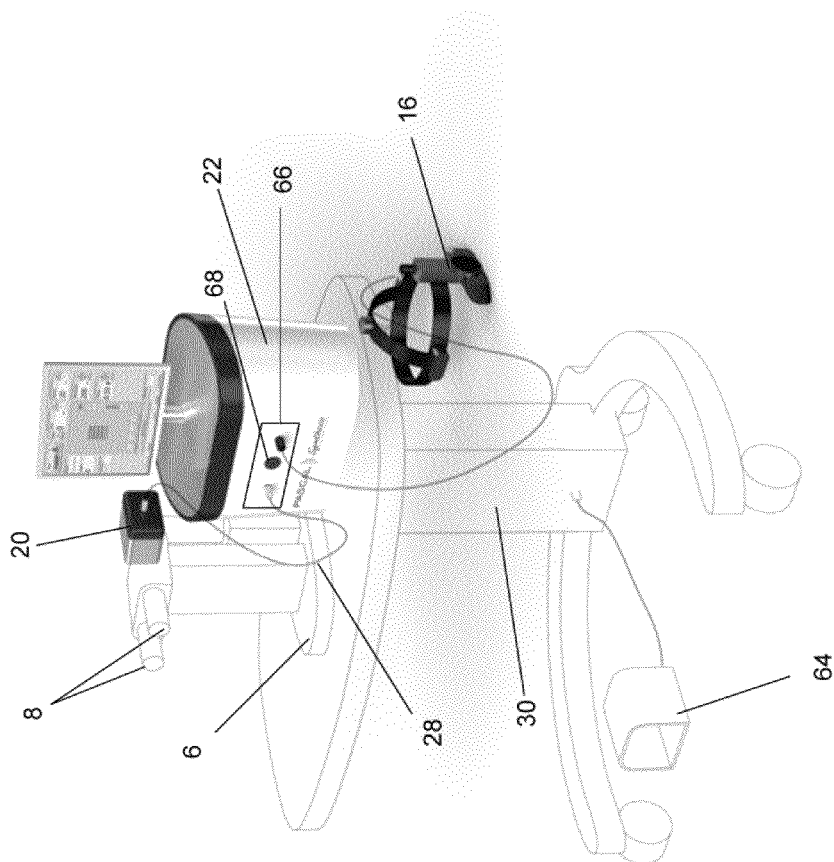
FIG. 10 illustrates aspects of an exemplary laser intervention system for the eye, wherein laser energy may be directed to a slit lamp and an LIO using coherent fiber bundles.

FIG. 10 illustrates another exemplary system configuration (1000) featuring a desktop-positioned proximal subsystem (22) coupled to a distal subsystem (20) via a coherent fiber bundle (28). The distal subsystem (20) is coupled to a slit lamp configuration (6) and may be utilized to deliver single treatment beams and patterned treatment beams to a patient's eye. Also shown as part of the proximal subsystem (22) is a coherent fiber bundle interface bus (66) that may be fed by scanning galvanometers and may be utilized to direct single treatment beams and patterned treatment beams to an LIO (16), endoprobe (not shown—port (68) may be used), or slit lamp proximal subsystem (20) through a coherent fiber bundle (28). In some examples, large (e.g., +/−18 degree) movements of the galvanometers may be used to select different fiber ports, while smaller movements may be used within the port to create patterns on the fiber. Alternatively, beam splitters within the proximal subsystem (22) may be utilized instead of the galvanometers. Another single beam bus (not shown) may be included to facilitate compatibility of the proximal subsystem (22) with conventional single beam LIO or endoprobe hardware, by enabling the proximal subsystem (22) to transmit a single laser beam through conventional multi-mode fibers to such devices.

Figure 11:
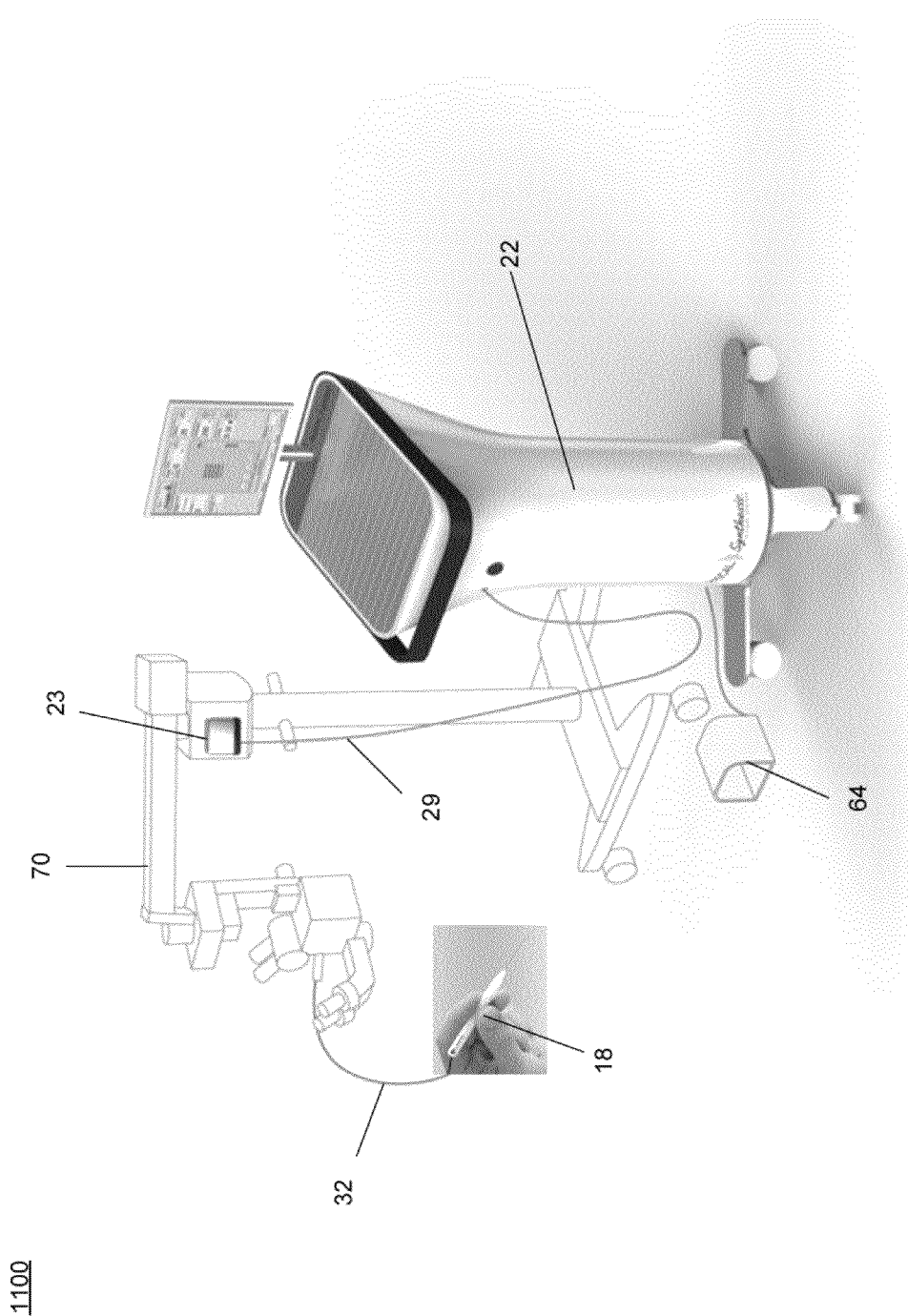
FIG. 11 illustrates aspects of an exemplary laser intervention system for the eye, wherein laser energy may be directed to a laser endoprobe using a coherent fiber bundle.

Referring to FIG. 11, an exemplary system configuration (1100) is depicted featuring a movably positioned proximal subsystem (22) coupled to an interface (23) with a coherent fiber bundle (29). The interface (23) may include couplings between coherent fiber bundles having the same or different sizes (e.g., same or different diameters or same or different number of pixels). The interface (23) is coupled to an operating room type microscope (70) and may be utilized to deliver single treatment beams and patterned treatment beams to a patient's eye through an additional section of coherent fiber bundle (32), which may be fixedly or removably coupled to the microscope arm and coupled ultimately to an endoprobe (18) comprising a distal subsystem (20) (not shown). Couplings between end-to-end (or cross sectional face to cross sectional face) portions of coherent fiber bundle may be accomplished efficiently using conventional 1:1 optical imager type hardware, featuring lenses such as traditional glass lenses, injection molded plastic lenses, reflective optics such as mirrors, GrIn (gradient index) lenses, diffractive lenses, and the like. Alternatively, other scaling factors may be used, for example, a larger (e.g., larger in diameter and having more pixels), permanently mounted fiber may be coupled to a smaller (e.g., smaller in diameter and having fewer pixels) endoprobe fiber to avoid pixel-to-pixel matching between the mating fibers. Disposables kits—such as for endoprobes, may, for example, comprise and endoprobe plus some nominal coupled length of coherent fiber bundle, such as 6 inches or so, and a ferrule type interface to work with a 1:1 optical imager configuration which preferably may be coupled to the distal end of the coherent fiber bundle which is coupled more proximally to either the distal subsystem (20) or proximal subsystem (22).

Figure 12:
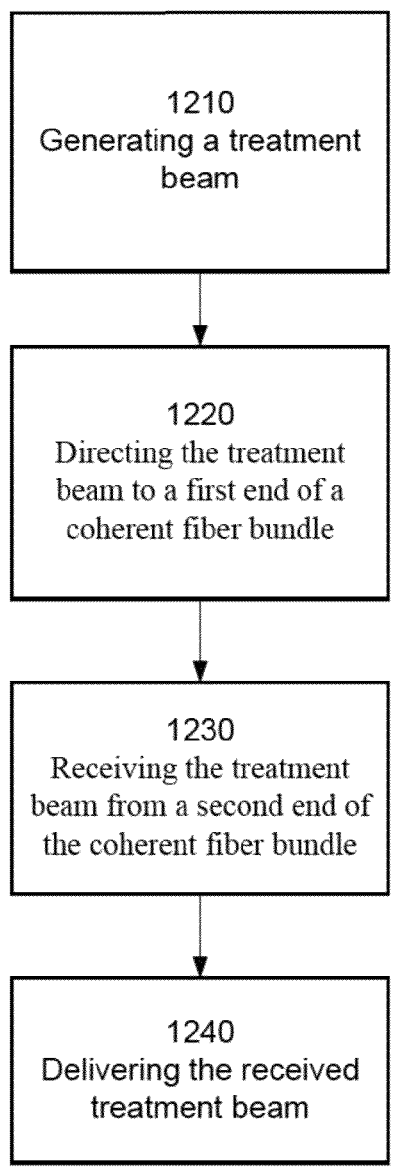
FIG. 12 illustrates an exemplary process for delivering therapeutic levels of laser energy through a coherent fiber bundle.

FIG. 12 illustrates an exemplary process (1200) for delivering therapeutic levels of laser energy through a coherent fiber bundle. At block (1210), a treatment beam may be generated. The treatment beam may have at least two separate areas of laser energy concentration (21), wherein a size of the at least two separate areas of laser energy concentration and a pattern formed by the at least two separate areas of laser energy concentration are adjustable by the first subsystem. This may be done, for example, using a subsystem similar or identical to proximal subsystem (22) of system (300). At block (1220), laser energy in the form of a treatment beam may be directed to a first end of a coherent fiber bundle similar or identical to coherent fiber bundles (28, 30, 32) of system (300). At block (1230) the treatment beam may be received from a second end of the coherent fiber bundle. In some examples, this may be done using a subsystem similar or identical to distal subsystem (20). At block (1240), the received treatment beam may be delivered to a patient. In some examples, the treatment beam may be delivered by a slit lamp, LIO, endoprobe, or the like, to generate a desired lesion pattern on the eye of a patient.

Various exemplary embodiments are described herein. Reference is made to these examples in a non-limiting sense. They are provided to illustrate more broadly applicable aspects of the disclosed technology. Various changes may be made and equivalents may be substituted without departing from the true spirit and scope of the various embodiments. In addition, many modifications may be made to adapt a particular situation, material, composition of matter, process, process act(s) or step(s) to the objective(s), spirit or scope of the various embodiments. Further, as will be appreciated by those with skill in the art that each of the individual variations described and illustrated herein has discrete components and features which may be readily separated from or combined with the features of any of the other several embodiments without departing from the scope or spirit of the various embodiments. All such modifications are intended to be within the scope of claims associated with this disclosure.

What is claimed is:

1. A system for laser treatment of an eye of a patient, the system comprising:
    a coherent fiber bundle comprising a first end and a second end;
    a first subsystem coupled to the first end of the coherent fiber bundle, the first subsystem configured to:
        generate a patterned treatment beam comprising at least two separate areas of laser energy concentration, wherein a size of the at least two separate areas of laser energy concentration and a pattern formed by the at least two separate areas of laser energy concentration are adjustable by the first subsystem; and
        direct the patterned treatment beam to the first end of the coherent fiber bundle; and
    a second subsystem coupled to the second end of the coherent fiber bundle, the second subsystem configured to:
        receive the patterned treatment beam from the second end of the coherent fiber bundle; and
        transmit the patterned treatment beam to the eye of the patient.

2. The system of claim 1, wherein the first subsystem is configured to direct the patterned treatment beam to a portion of the first end of the coherent fiber bundle, and wherein the second subsystem is configured to receive the patterned treatment beam from a portion of the second end of the coherent fiber bundle, the portion of the second end of the coherent fiber bundle corresponding to the portion of the first end of the coherent fiber bundle.

3. The system of claim 2, wherein a relative location of the portion of the first end of the coherent fiber bundle with respect to the first end of the coherent fiber bundle is substantially the same as a relative location of the portion of the second end of the coherent fiber bundle with respect to the second end of the coherent fiber bundle.

4. The system of claim 1, wherein the treatment beam is at a non-visible wavelength.

5. The system of claim 1, wherein the treatment beam has a power in the range of 30 mW to 2 W.

6. The system of claim 1, wherein the first subsystem comprises:
    a laser source configured to generate a laser beam;
    a spot size selector configured to:
        receive the laser beam; and
        adjust the size of the at least two separate areas of laser energy concentration by adjusting the size of the laser beam; and
    scanning hardware configured to:
        receive the size-adjusted laser beam from the spot size selector; and
        generate the pattern formed by the at least two separate areas of laser energy concentration by selectively redirecting the received size-adjusted laser beam.

7. The system of claim 6, wherein the laser source is further configured to generate an alignment beam having an average power of less than 1.2 mW and at a visible wavelength.

8. The system of claim 6, wherein the scanning hardware comprises a collimating lens and a scanning device.

9. The system of claim 8, wherein the scanning device comprises a galvanometer, micro-electro-mechanical ("MEMS") device, or rotating polygon.

10. The system of claim 1, wherein the first subsystem further comprises an interface for coupling to an LIO or endoprobe via a multi-mode fiber, the interface configured to transmit a single treatment beam through the multi-mode fiber.

11. The system of claim 1, wherein the first subsystem is contained in a first housing that is physically separate from a second housing containing the second subsystem.

12. The system of claim 1, wherein the second subsystem is incorporated within a slit lamp, endoprobe, or laser indirect ophthalmoscope ("LIO").

13. The system of claim 12, wherein the second subsystem is coupled to a slit lamp, endoprobe, or LIO.

14. The system of claim 1, wherein the second subsystem comprises a field adjustment module for adjusting a field of view.

15. A method for laser treatment of an eye of a patient, the method comprising:
    generating, by a first subsystem, a treatment beam comprising at least two separate areas of laser energy concentration, wherein a size of the at least two separate areas of laser energy concentration and a pattern formed by the at least two separate areas of laser energy concentration are adjustable by the first subsystem; and directing, by the first subsystem, the patterned treatment beam to a first end of a coherent fiber bundle;

receiving, by a second subsystem, the patterned treatment beam from a second end of the coherent fiber bundle;

delivering the patterned treatment beam to the eye of the patient.

16. The method of claim 15, wherein the patterned treatment beam is directed to a portion of the first end of the coherent fiber bundle, and wherein the patterned treatment beam is received from a portion of the second end of the coherent fiber bundle, the portion of the second end of the coherent fiber bundle corresponding to the portion of the first end of the coherent fiber bundle.

17. The method of claim 16, wherein a relative location of the portion of the first end of the coherent fiber bundle with respect to the first end of the coherent fiber bundle is substantially the same as a relative location of the portion of the second end of the coherent fiber bundle with respect to the second end of the coherent fiber bundle.

18. The method of claim 15, wherein the patterned treatment beam is at a non-visible wavelength.

19. The method of claim 15, wherein the patterned treatment beam has a power in the range of 30 mW to 2 W.

20. The method of claim 15, wherein the first subsystem comprises:
   a laser source configured to generate a laser beam;
   a spot size selector configured to:
      receive the laser beam; and
      adjust the size of the at least two separate areas of laser energy concentration by adjusting the size of the laser beam; and
   scanning hardware configured to:
      receive the size-adjusted laser beam from the spot size selector; and
      generate the pattern formed by the at least two separate areas of laser energy concentration by selectively redirecting the received size-adjusted laser beam.

21. The method of claim 20, wherein the laser source is further configured to generate an alignment beam having an average power of less than 1.2 mW and at a visible wavelength.

22. The method of claim 15, wherein the second subsystem is incorporated within a slit lamp, endoprobe, or LIO.

23. The method of claim 22, wherein the second subsystem is coupled to a slit lamp, endoprobe, or LIO.

24. The method of claim 15, wherein the second subsystem comprises a field adjustment module for adjusting a field of view.

* * * * *

UNITED STATES PATENT AND TRADEMARK OFFICE
CERTIFICATE OF CORRECTION

| | | |
|---|---|---|
| PATENT NO. | : 8,591,501 B2 | Page 1 of 1 |
| APPLICATION NO. | : 13/042429 | |
| DATED | : November 26, 2013 | |
| INVENTOR(S) | : David Mintz et al. | |

It is certified that error appears in the above-identified patent and that said Letters Patent is hereby corrected as shown below:

Title Page: Item 74

Delete "Morris" and insert --Morrison--.

Signed and Sealed this
Twenty-fifth Day of February, 2014

Michelle K. Lee
*Deputy Director of the United States Patent and Trademark Office*